US00PP31331P3

(12) United States Plant Patent
Kleinwee

(10) Patent No.: US PP31,331 P3
(45) Date of Patent: Jan. 7, 2020

(54) ***PETUNIA* PLANT NAMED 'PEHY0038'**

(50) Latin Name: *Petunia hybrida*
Varietal Denomination: PEHY0038

(71) Applicant: SYNGENTA PARTICIPATIONS AG, Basel (CH)

(72) Inventor: Theodorus Cornelis Maria Van Kleinwee, Andijk (NL)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 15/998,216

(22) Filed: Jul. 18, 2018

(65) Prior Publication Data

US 2019/0200501 P1 Jun. 27, 2019

(30) Foreign Application Priority Data

Dec. 22, 2017 (EM) ..... 2017/3382

(51) Int. Cl.
*A01H 5/02* (2018.01)
*A01H 6/82* (2018.01)

(52) U.S. Cl.
USPC ..... Plt./356.13
CPC ..... *A01H 6/824* (2018.05)

(58) Field of Classification Search
USPC ..... Plt./356.13, 356.1
CPC ..... A01H 6/824; A01H 5/02
See application file for complete search history.

*Primary Examiner* — Keith O. Robinson
(74) *Attorney, Agent, or Firm* — Dale Skalla

(57) ABSTRACT

A new *Petunia* plant named 'PEHY0038' particularly distinguished by its medium sized, white with blue edge flowers, medium to late flowering and a mounding plant habit.

1 Drawing Sheet

Latin name of the genus and species of the plant claimed: *Petunia hybrida.*

Varietal denomination: 'PEHY0038'.

BACKGROUND OF THE NEW PLANT

The present invention comprises a new *Petunia*, botanically known as *Petunia hybrida*, and hereinafter referred to by the variety name 'PEHY0038'.

'PEHY0038' is a product of a planned breeding program. The new cultivar has medium sized, white with blue edge flowers, medium to late flowering and a mounding plant habit.

'PEHY0038' originated from a hybridization made in October 2013 in a controlled breeding environment in Enkhuizen, The Netherlands. The female parent was the proprietory line 'N2848-1' (not patented). Compared to 'PEHY0038', it has a comparable plant habit and vigor, is earlier, has a bigger flower and has a white flower color with rose edge.

The male parent of 'PEHY0038' was the unpatented proprietary line 'N2280-1', a plant with a more semi-trailing plant habit, earlier flowering and a white flower color with blue veins.

The resulting seeds were sown in January 2014. 'PEHY0038' was selected as one flowering plant within the progeny of the stated cross in May, 2014 in a controlled environment in Enkhuizen, The Netherlands.

The first act of asexual reproduction of 'PEHY0038' was accomplished when vegetative stem cuttings were propagated from the initial selection in June 2014 in a controlled environment in Angers, France.

BRIEF SUMMARY OF INVENTION

Horticultural examination of plants grown from cuttings of the plant initiated in June 2014 and continuing thereafter, has demonstrated that the combination of characteristics as herein disclosed for 'PEHY0038' are firmly fixed and are retained through successive generations of asexual reproduction.

'PEHY0038' has not been observed under all possible environmental conditions. The phenotype may vary significantly with variations in environment such as temperature, light intensity, and day length.

A Plant Breeder's Rights for this cultivar was applied for in the European Union on Dec. 22, 2017, No. 2017/3382. 'PEHY0038' has not been made publicly available prior to the effective filing date of this application, notwithstanding any disclosure that may have been made less than one year prior to the effective filing date of this application by the inventor or another who obtained 'PEHY0038' directly from the inventor.

The following traits have been repeatedly observed and are determined to be basic characteristics of the new variety. The combination of these characteristics distinguishes this *Petunia* as a new and distinct variety.

BRIEF DESCRIPTION OF THE PHOTOGRAPHS

The accompanying photographic drawings show typical flower and foliage characteristics of 'PEHY0038' with colors being as true as possible with an illustration of this type.

Figure 1:
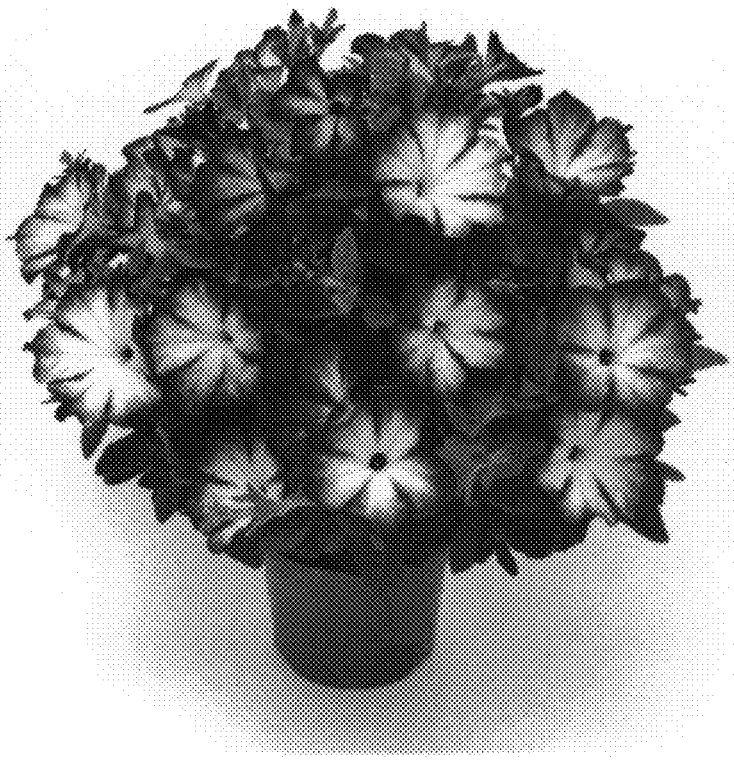
Figure 2:
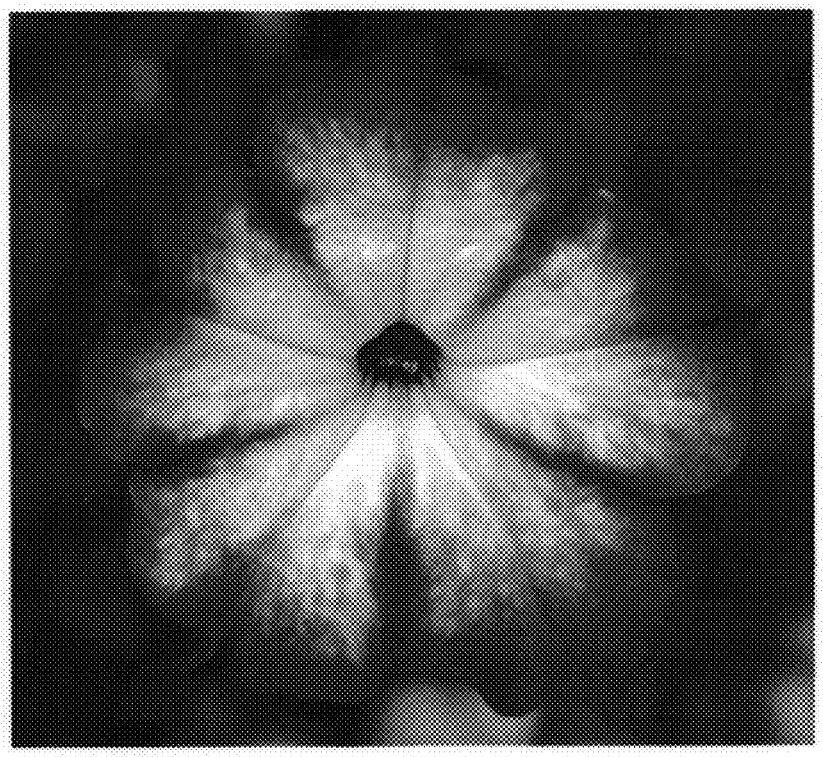

The photographic drawings show in FIG. 1. a flowering plant of the new variety and in FIG. 2. a close-up of the flowers.

DETAILED BOTANICAL DESCRIPTION

The aforementioned photographs were taken in September 2017 from plants growing outside in containers in Andijk, The Netherlands. These plants were approximately 20 weeks of age.

The plant descriptions and measurements were taken in September 2017 in Andijk, The Netherlands on approximately 20 week old plants that were growing in containers.

Color references are made to The Royal Horticultural Society Colour Chart (R.H.S.) 2001.

TABLE 1

DIFFERENCES BETWEEN THE NEW VARIETY 'PEHY0038' AND A SIMILAR VARIETY

| | 'PEHY0038' | 'PEHY0013' (U.S. Plant Pat. No. 28,029) |
|---|---|---|
| Plant habit: | Upright | Mounding to trailing |
| Flower color: | White with blue edge | White with blue edge, changing to violet when exposed to high light |
| Branching: | Very good branching | Moderate branching |
| Flower size: | Medium | Large |

Plant:

*Form, growth and habit.*—Semi-trailing plant habit.

*Plant height.*—32 cm.

*Plant height (inflorescence included).*—37 cm.

*Plant diameter (width).*—Approximately 40 cm.

Roots:

*Number of days to initiate and produce roots.*—16 days at about 22° C.

*Type.*—Fine, fibrous, free branching.

*Color.*—RHS N158D.

Foliage:

*Arrangement.*—Alternate, simple; sometimes opposite, decussate.

*Immature leaf, color upper surface.*—RHS 146B.

*Immature leaf, color lower surface.*—RHS 146A.

*Mature leaf, color upper surface.*—RHS 137A.

*Mature leaf, color lower surface.*—RHS 146A.

*Variegation of the leaf.*—Absent.

*Length.*—2.8-3 cm.

*Width.*—1.4 cm.

*Shape.*—Ovate.

*Base shape.*—Shortly attenuate.

*Apex shape.*—Acute.

*Margin.*—Entire.

*Texture, upper surface.*—Densely covered with short hair.

*Lower surface.*—Densely covered with short hairs.

*Color of veins, upper surface.*—RHS 144C.

*Color of veins, lower surface.*—RHS 144C.

*Conspicuousness of the veins of the flower.*—Absent.

*Petiole color.*—RHS 144C.

*Length.*—0.3 cm.

*Diameter.*—0.3 cm.

*Petiole texture.*—Densely covered with short hairs.

Stem:

*Quantity of main branches per plant.*—4-5.

*Color of stem.*—RHS 144C.

*Length of stem.*—30 cm.

*Diameter.*—0.3 cm.

*Length of internodes.*—3-4 cm.

*Texture.*—Dense, mostly glandular short hairs.

*Color of pedicel.*—RHS 144C.

*Length of pedicel.*—1.3-2.0 cm.

*Diameter of pedicel.*—0.2 cm.

*Texture of pedicel.*—Densely covered with short hairs.

Inflorescence:

*Type.*—Flowers solitary in upper leaf axis.

*Floret type.*—Funnel-shaped; 5 lobed petals; fused at base.

*Blooming habit.*—Medium to late flowering in greenhouse, flowering throughout the summer months.

*Quantity of inflorescences per plant.*—Approximately 25.

*Lastingness of individual blooms on the plant.*—About 7 days.

*Fragrance.*—Present, spicy.

Bud (just when opening):

*Color.*—RHS N79A at top, RHS N79D with veins RHS 143A towards base.

*Length.*—3.5 cm.

*Width.*—3.1 cm.

*Shape.*—Oblong.

Immature inflorescence:

*Flower horizontal diameter.*—5.1 cm.

*Color petals, upper surface.*—Darker than RHS 83A to RHS 83B, lighter towards throat, up to whiter than RHS 155A.

*Color petals, lower surface.*—RHS 83C with veins RHS N92.

Mature flower:

*Flower horizontal diameter.*—6 cm.

*Flower height (vertical).*—2.5-3.5 cm.

*Color upper surface.*—RHS 88A, lighter towards throat, up to whiter than RHS 155A.

*Color lower surface.*—RHS 83C with veins RHS N92.

*Apex shape.*—Rounded to slightly acuminate.

*Margin.*—Entire.

*Waviness of margin.*—Medium.

*Petal lobation.*—Weak.

*Petal texture, upper surface.*—Bearing, covered with or resembling smooth.

*Petal texture, lower surface.*—Some glandular hairs, more dense on veins.

*Corolla tube color outside.*—RHS 79D.

*Corolla tube color inside.*—Longitudinal striped; RHS 88A and RHS 158D. At base some RHS 157B coloration.

*Corolla tube length.*—2.6 cm.

*Corolla tube texture, outside.*—Rather dense and short glandular hairs.

*Corolla tube texture, inside.*—Glabrous.

Calyx:

*Color of sepal, upper surface.*—RHS 146A.

*Color of sepal, lower surface.*—RHS 146B.

*Length.*—2.0 cm.

*Width.*—0.5 cm.

*Shape.*—Ensiform.

*Apex shape.*—Acute.

*Base.*—Fused.

*Margins.*—Entire.

*Texture, upper surface.*—Densely covered with short glandular hairs.

*Lower surface.*—Densely covered with short glandular hairs.

Reproductive organs:

*Pistil.*—1.

*Length.*—2.6 cm.

*Style color.*—RHS 91C.

*Style length.*—1.3 cm.

*Stigma color.*—RHS 145A.

*Stamens.*—
*Quantity per flower.*—5.
*Color of filaments.*—RHS 157C.
*Length filaments.*—2.3 cm.
*Anther color.*—RHS 91C.
*Anther length.*—0.2 cm.
*Anther shape.*—Elliptical.
*Color of pollen.*—RHS 92C.
*Pollen amount.*—Abundant.
*Fertility/seed set.*—Has not been observed on this hybrid.
*Disease/pest resistance.*—Has not been observed on this hybrid.

What is claimed is:

1. A new and distinct variety of *Petunia* plant named 'PEHY0038' substantially as illustrated and described herein.

* * * * *